(12) United States Patent
Bognár et al.

(10) Patent No.: US 9,884,040 B2
(45) Date of Patent: Feb. 6, 2018

(54) DESETHYLAMIODARONE FOR USE IN CANCER TREATMENT

(71) Applicant: PÉCSI TUDOMÁNYEGYETEM, Pécs (HU)

(72) Inventors: Zita Bognár, Pellérd (HU); Balázs Sümegi, Pécs (HU); Ferenc Gallyas, Jr., Pécs (HU); Kálmán Tóth, Pécs (HU)

(73) Assignee: Pésci Tudományegyetem, Pécs (HU)

( * ) Notice: Subject to any disclaimer, the term of this patent is extended or adjusted under 35 U.S.C. 154(b) by 0 days.

(21) Appl. No.: 15/363,001

(22) Filed: Nov. 29, 2016

(65) Prior Publication Data
US 2017/0151211 A1    Jun. 1, 2017

Related U.S. Application Data

(60) Provisional application No. 62/260,675, filed on Nov. 30, 2015.

(30) Foreign Application Priority Data

Nov. 30, 2015  (EP) ..................................... 15197046

(51) Int. Cl.
*A61K 31/343*    (2006.01)

(52) U.S. Cl.
CPC ................................. *A61K 31/343* (2013.01)

(58) Field of Classification Search
CPC .................................................... A61K 31/343
See application file for complete search history.

(56) References Cited

U.S. PATENT DOCUMENTS

2007/0179152 A1*  8/2007  Lee ........................ A61K 31/36
                                                514/254.01

OTHER PUBLICATIONS

Chauffert et al. Br. J. Cancer (1987), 56 p. 119-122.*
Van Der Graaf et al.: "In Vitro and in Vivo Modulation of Multi-Drug Resistance With Amiodarone", Int. J. Cancer, 1991, vol. 48, pp. 616-622.

* cited by examiner

*Primary Examiner* — Yong L Chu
(74) *Attorney, Agent, or Firm* — Jason D. Voight

(57) ABSTRACT

The invention relates to a compound selected from the group consisting of desethylamiodarone and pharmaceutically acceptable salts, hydrates and solvates thereof, as well as pharmaceutical composition comprising the compound together with a pharmaceutically acceptable excipient, vehicle or carrier, for use in the treatment of cancer.

4 Claims, 13 Drawing Sheets

C

D

DESETHYLAMIODARONE FOR USE IN CANCER TREATMENT

This application claims priority to provisional application No. 62/260,675, filed Nov. 30, 2015, the entire disclosure of which is hereby incorporated by reference herein.

BACKGROUND OF INVENTION

Desethylamiodarone (2-butyl-3-benzofuranyl)[4-[2-(ethylamino)ethoxy]-3,5-diiodophenyl]-methanone, DEA), the major metabolite of the widely used antiarrhythmic drug amiodarone (AM), also has antiarrhythmic activity, significantly increasing the action potential duration (class III antiarrhythmic effect) and decreasing the maximum rate of depolarization (class I antiarrhythmic effect) at clinically relevant concentrations. (1, 2) Amiodarone is widely used in the treatment of a variety of cardiac diseases. (3, 4, 5) Amiodarone and its main metabolite DEA are both strongly bound to plasma proteins. (6) DEA rapidly accumulates in extra cardiac tissues (especially in the lungs) after amiodarone treatment, sometimes in higher concentrations than amiodarone itself. (7, 8, 9, 10) Tissue concentrations of AM and of DEA are 100 to above 1000 times higher than the corresponding plasma concentrations. (11) Organs that store these drugs are adipose tissue, liver and lung, but also skin, pancreas, myocardium and thyroid gland. Except in the adipose tissue, the tissue concentrations of the metabolite are higher than that of the parent drug following chronic administration of AM. (12) Repetitive exposures of cell cultures to AM and DEA respectively resulted in a cumulative and partially saturable drug uptake. Under all conditions tested DEA accumulation was always higher than that of AM. (13) The mean elimination half-life of DEA is 40 days and varies considerably between individuals. (14) Direct and indirect evidence for intralysosomal localization have been presented for AM and DEA in vivo and in vitro. (15) The therapeutic range of amiodarone has been recommended to be <5.7 µM (16). Indeed, it has been reported that the concentrations of amiodarone and DEA in patient plasma are 1.6-5.3 µM and 1.7-4.5 µM, respectively. (17) Amiodarone was found to activate mainly necrotic cell death pathways, whereas DEA also activated apoptotic pathways. (18) DEA may act synergistically with amiodarone. (19) DEA has greater cytotoxic potency in vitro compared to AM (20), however this toxic effect is further enhanced in the presence of amiodarone. To avoid this enhanced toxic effect, as well as to decrease the likeliness of the side effects we will perform our experiments exclusively with DEA. After administration of amiodarone in therapeutic doses, plasma concentration of DEA is in a range of 1.7-4.5 µM (17), however in the lungs DEA can reach mM concentrations due to its significant accumulation in that organ. (21)

Modern surgical techniques and new chemotherapeutic approaches have significantly improved the effectiveness of treatment in primary tumors, but metastasis remains the leading cause of death in patients with cancer. (22) In determining the stage, relevant treatment, and prognosis of most solid cancers metastasis is the key factor. Tumor metastasis is a complex process that involves local invasion, intravasation, and survival in the circulation, extravasation, and colonization. The tumor cells must overcome numerous hurdles to successfully colonize in the target organ (23, 24) Lung metastases are identified in 30-55% of all cancer patients, though prevalence varies based on the type of primary cancer. Almost any cancer has the ability to spread to the lungs, but the tumors that most commonly do so include bladder cancer, colon cancer, breast cancer, prostate cancer, sarcoma, Wilms tumor, and neuroblastoma. (23, 24) The lungs are the most common site of metastasis in melanoma (22). Although metastasis only occurs in approximately 10% of melanoma patients, it remains the major cause of death (25).

The present inventors surprisingly found that DEA has significant anti-tumor effect. Although DEA is a well-known metabolite, which accumulates in lungs, and is capable of inducing apoptotic cell death, no such anti-tumor effect has been suggested.

DETAILED DESCRIPTION OF THE INVENTION

The present invention provides a pharmaceutical composition comprising a compound selected from the group consisting of desethylamiodarone (DEA) and pharmaceutically acceptable salts, hydrates and solvates thereof, together with a pharmaceutically acceptable excipient, vehicle and/or carrier, for use in the treatment of a proliferative disorder.

The present invention further provides a method for the treatment of a proliferative disorder, comprising the step of administering a pharmaceutical composition comprising a compound selected from the group consisting of desethylamiodarone (DEA) and pharmaceutically acceptable salts, hydrates and solvates thereof, together with a pharmaceutically acceptable excipient, vehicle and/or carrier.

In a preferred embodiment, the proliferative disorder is cancer.

In another preferred embodiment, the composition is administered with one or more anticancer therapies.

In another preferred embodiment, the one or more anticancer therapy is selected from the group consisting of surgery, radiotherapy, and chemotherapy.

In another preferred embodiment, the composition is administered together with one or more bioactive agents.

In another preferred embodiment, the bioactive agents are selected from a group consisting of antibodies, growth factors, hormones, cytokines, anti-hormones, xanthines, interleukins, interferons, and cytotoxic agents.

In another preferred embodiment, the cytotoxic agent is selected from the group consisting of doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, adriamycin, cisplatin, camoplatin, cyclophosphamide, dacarbazine, vinblastine, vincristine, mitoxantrone, bleomycin, mechlorethamine, prednisone, procarbazine methotrexate, flurouracils, etoposide, taxol, taxal analogs, and mitomycin.

In another preferred embodiment, the composition is administered together with, prior to, or subsequent to the administration of one or more combinations of cytotoxic agents as part of a treatment regimen, wherein the combination of cytotoxic agents is selected from:

A. CHOPP (cyclophosphamide, doxorubicin, vincristine, prednisone, and procarbazine);

B. CHOP (cyclophosphamide, doxorubicin, vincristine, and prednisone);

C. COP (cyclophosphamide, vincristine, and prednisone);

D. CAP-BOP (cyclophosphamide, doxorubicin, procarbazine, bleomycin, vincristine, and prednisone);

E. m-BACOD (methotrexate, bleomycin, doxorubicin, cyclophosphamide, vincristine, dexamethasone, and leucovorin);

F. ProMACE-MOPP (prednisone, methotrexate, doxorubicin, cyclophosphamide, etoposide, leucovorin, mechloethamine, vincristine, prednisone, and procarbazine);

G. ProMACE-CytaBOM (prednisone, methotrexate, doxorubicin, cyclophosphamide, etoposide. teucovorin, cytarabine, bleomycin, and vincristine);

H. MACOP-B (methotrexate, doxorubicin, cyclophosphamide, vincristine, prednisone, bleomycin, and leucovorin);

I. MOPP (mechloethamine, vincristine, prednisone, and procarbazine);

J. ABVD (adriamycin/doxorubicin, bleomycin, vinblastine, and dacarbazine);

K. MOPP (mechloethamine, vincristine, prednisone, and procarbazine) alternating with ABV (adriamycin/doxorubicin, bleomycin, and vinblastine);

L. MOPP (mechloethamine, vincristine, prednisone, and procarbazine) alternating with ABVD (adriamycin/doxorubicin, bleomycin, vinblastine, and dacarbazine);

M. ChlVPP (chlorambucil, vinblastine, procarbazine, and prednisone);

N. IMVP-16 (ifosfamide, methotrexate, and etoposide);

O. MIME (methyl-gag, ifosfamide, methotrexate, and etoposide);

P. DHAP (dexamethasone, high-dose cytarabine, and cisplatin);

Q. ESHAP (etoposide, methylpredisolone, high-dose cytarabine, and cisplatin);

R. CEPP(B) (cyclophosphamide, etoposide, procarbazine, prednisone, and bleomycin);

S. CAMP (lomustine, mitoxantrone, cytarabine, and prednisone);

T. CVP-1 (cyclophosphamide, vincristine, and prednisone);

U. ESHOP (etoposide, methylpredisolone, high-dose cytarabine, vincristine and cisplatin);

V. EPOCH (etoposide, vincristine, and doxorubicin for 96 hours with bolus doses of cyclophosphamide and oral prednisone);

W. ICE (ifosfamide, cyclophosphamide, and etoposide);

X. CEPP(B) (cyclophosphamide, etoposide, procarbazine, prednisone, and bleomyan);

Y. CHOP-B (cyclophosphamide, doxorubicin, vincristine, prednisone, and bleomycin); and Z. P/DOCE (epirubicin or doxorubicin, vincristine, cyclophosphamide, and prednisone).

In another preferred embodiment, the cancer is cutaneous or intraocular melanoma, mesothelioma, renal cell carcinoma, breast cancer, head and neck cancer, a primary or secondary brain tumor, carcinoma of the cervix, cancer of the urethra, prostate cancer, pancreatic cancer, testicular cancer, hepatobiliary cancer, hepatic duct cancer, biliary duct cancer, colorectal cancer, bladder cancer, ovarian cancer, lung cancer, non-small cell lung cancer, small cell lung cancer, colon cancer, rectal cancer, or cancer of the anal region. In a particularly preferred embodiment, the cancer is selected from the group consisting of lung cancer, urinary bladder carcinoma, melanoma, mammary carcinoma, cervical cancer, and the metastasis thereof.

The prior art has not suggested the use of DEA for the treatment of proliferative disorders. WO2004105696 relates to the treatment of neoplasms, and amiodarone is mentioned as a compound the anti-proliferative effects are enhanced by the disclosed triazole compounds. DEA is mentioned as a related compound to amiodarone, but no treatment is disclosed, especially not for DEA alone, in this document.

Van der Graaf et al. (Int. J. Cancer, vol. 48, pp. 616-22, 1991) disclose that DEA can induce an increase in the cytotoxicity of adriamicin.

In the current invention, we report the ability of an amiodarone metabolit, desethyamiodarone, to inhibit growth and induce apoptosis in several type of cancer cells, which indicates its potential as an antitumor agent for the treatment of cancer. Desethylamiodarone (DEA) is the main metabolite of the widely used anti-arrhythmic drug amiodarone. DEA also has antiarrhythmic activity in clinical relevant concentration. (1, 2) Our previous results showed that DEA caused mitochondrial permeability transition and induced apoptotic cell death. (27, 28, 29, 30) DEA accumulates rapidly in the lungs. (7, 8) DEA seemed to act synergistically with amiodarone. (19) We used DEA and not amiodarone for the experiments planned. Using DEA we exactly know the dose which was given and we do not have to worry about this synergic cytotoxicity. Here, we checked whether Desethylamiodarone can affect invasion, migration of cancer cells. First of all, we initially checked whether desethylamiodarone has effect on the viability of T24 (human urinary bladder carcinoma), B16F10 (mice melanoma), 4T1 (mouse mammary carcinoma) cells using MTT assay. As shown in FIG. 1-3 Desethylamiodarone had significant cytotoxic activity in very low concentrations. To assess the recovery ability of cells that survived treatment, long-term (7 days) colony formation assay was performed. As shown in FIG. 5-8 one week following treatment with desethylamiodarone indicated already a significant decrease in the number and the size of colonies in T24 (human urinary bladder carcinoma), B16F10 (mice melanoma), 4T1 (mouse mammary carcinoma) A549 (human lung adenocarcinoma epithelial), HeLa (human cervix adenocarcinoma) cell lines.

Metastasis is fundamental property of malignant cancer cells, and occurs through a series of sequential steps including invasion, intravasation, survival and translocation in the circulation system, extravasation and survival in new organ. Cancer recurrence by metastasis is one of the main causes of mortality in cancer patients and is currently a main target for cancer therapy (31) Furthermore, metastasis causes about 90% of human cancer-associated deaths (32, 33, 34). Thus, a number of researchers are investigating molecular mechanisms related to cancer metastasis, and searching drugs which can suppress metastatic potential of cancer. We began to detect the antimetastatic ability of DEA in vivo; thus, we performed experimental lung metastasis tests. The results show that DEA can significantly reduce the number of tumor nodules and decrease lung weight. Therefore, DEA has a significant anti-metastatic effect in vivo. In addition, the number of cancer nodules in the lungs of DEA-treated mice was significantly reduced by injecting B16F10 cells.

PI3K/Akt pathway plays an important role in cell division, apoptosis and tumourigenesis. PI3K is a lipid second messenger of intracellular signal transduction, and Akt is its main target. Phosphorylated Akt possesses a wide range of biological effects, such as anti-apoptotic and cell survival-promoting activity (35) Consistent activation of the PI3K/Akt pathway has been detected in numerous human tumor cells, including breast cancer, bladder cancer (36, 37). This signal pathway promotes tumor survival, progression and metastasis (36, 37). Akt regulates several cellular activities, including proliferation, the cell cycle and apoptosis (38). In the current study, we demonstrated that DEA repressed Akt phosphorylation in a concentration and time-dependent manner DEA is a direct inhibitor and can interfere with the activation of PI3K/Akt. The pro-apoptotic effect of DEA might be due to its ability to induce BCL-2 degradation and enhance the expression of Bax and P53. We therefore determined whether DEA-induced decreased AKT phosphorylation leads to changes in GSK-3β phosphorylation in T24 bladder carcinoma. We found that the decrease in AKT phosphorylation after treatment with DEA new as accompanied by decrease in GSK-3β phosphorylation. PI3K/AKT and MAPK/ERK pathways activation have been regarded as important key players in cancer carcinogenesis (39). However, only limited data on their effects have been published thus far.

B-cell-specific moloney murine leukemia virus integration site 1 (BMI1) is a transcriptional repressor of polycomb repressive complex 1(PRC1), which is located at chromosome 10p11.23. It plays an essential role in embryogenesis and maintenance adult stem cell's self-renewal. BMI1 was originally identified as an oncogene which was associated with c-myc in the generation and development of mouse pre B-cell lymphomas. There is a body of evidences suggesting that BMI1 is involved in the proliferation, senescence, migration, and tumorigenesis of cancer. Experimental researchers have convincingly linked BMI1 to tumorigenesis. High expression of BMI1 was associated with aggressive tumor behavior and poor outcome (40).

There is increasing evidence that a variety of cancers arise from transformation of normal stem cells to cancer stem cells (CSCs). CSCs are thought to sustain cancer progression, invasion, metastasis, and recurrence after therapy. Reports suggest that CSCs are highly resistant to conventional therapy. Emerging evidences show that the chemoresistance of CSCs are in part due to the activation of B cell-specific Moloney murine leukemia virus integration site 1 (BMI1), a stem cell factor, and a polycomb group family member. BMI1 is reported to regulate the proliferation activity of normal, stem, and progenitor cells. BMI1 plays a role in cell cycle, cell immortalization, and senescence. Numerous studies demonstrate that BMI1, which is upregulated in a variety of cancers, has a positive correlation with clinical grade/stage and poor prognosis. Although evidences are in support of the role of BMI1 as a factor in chemoresistance displayed by CSCs, its mechanism of action is not fully understood (41).

Due to the fact that DEA inhibits the growth of tumor cells, reduce their colony forming potential, induces cell death and significantly increases the high energy irradiation induced cell death, the invention is useful in the treatment of cancer and increases the efficacy of the high energy irradiation in cancer treatment. The molecular mechanisms of desethylamiodarone among other possible effects is the inhibition of cytoprotective PI-3-K-Akt and ERK1/2 pathways which play significant role in cell death and radiosensitization.

In certain embodiments, DEA reduces Akt activity and ERK1/2 activities contributing to cell death (FIG. 2) and reduces the colony formation (FIG. 5) and so metastases formation of bladder cancer cell, so improves bladder cancer therapy.

In certain other embodiments, DEA reduces Akt activity and ERK1/2 activities contributing to cell death (FIG. 3) and reduces the colony formation (FIG. 6) and so metastases formation of melanoma cell, so improves metastatic melanoma therapy.

In certain other embodiments, DEA reduces Akt activity and ERK1/2 activities contributing to cell death (FIG. 4) and reduces the colony formation and so metastases formation of breast cancer cell, so improves breast cancer therapy.

In certain other embodiments, DEA reduces Akt activity and ERK1/2 activities contributing to cell death and reduces the colony formation (FIG. 7) and so metastases formation of lung cancer cell, so improves lung cancer therapy.

In certain other embodiments, DEA reduces Akt activity and ERK1/2 activities contributing to cell death and reduces the colony formation (FIG. 8) and so metastases formation of cervix cancer cell, so improves cervix cancer therapy.

In a preferred embodiment of the invention, DEA may be used in conjunction with radiotherapy. Standard protocols may be adapted easily by the person skilled in the art to combine the DEA therapy with the state of the art radiotherapy regimens.

In certain other embodiments, DEA through the reduction of Akt activity and ERK1/2 activities, contributing to its radiosensitizing effects (FIG. 9) making a more effective bladder cancer therapy as radiosensitizer.

In certain other embodiments, DEA through the reduction of Akt activity and ERK1/2 activities contributing to its radiosensitizing effects (FIG. 10) making a more effective lung cancer therapy as radiosensitizer.

In certain other embodiments, DEA through the reduction of Akt activity and ERK1/2 activities contributing to its radiosensitizing effects (FIG. 11) making a more effective cervix cancer therapy as radiosensitizer.

In certain other embodiments, DEA provides a suitable adjunct to enhance efficacy of radiotherapy in models of metastatic melanome (B16F10 cell line) by reducing cancer stem cell formation determined from significantly reduced spheroid numbers, and decreased the number of cells with CD133, CD24 and CD44 cancer stem cell markers.

In certain other embodiments, DEA provides a suitable adjunct to enhance efficacy of radiotherapy in models of metastatic bladder cancer (T24 cell line) by reducing cancer stem cell formation determined from significantly reduced spheroid numbers, and decreased the number of cells with CD133, CD24 and CD44 cancer stem cell markers.

In certain other embodiments, DEA provides a suitable adjunct to enhance efficacy of radiotherapy in models of breast cancer (4T1 mouse mammary carcinoma cell line) by reducing cancer stem cell formation determined from significantly reduced spheroid numbers, and decreased the number of cells with CD133, CD24 and CD44 cancer stem cell markers.

In certain other embodiments, DEA provides a suitable adjunct to enhance efficacy of radiotherapy in models of pancreatic tumors (Panc-1 cell line) by reducing cancer stem cell formation determined from significantly reduced spheroid number, and decreased the number of cells with CD13, CD44 and CD24 cancer stem cell markers.

In a preferred embodiment of the invention, DEA may be used in conjunction with surgery. The attending physicians will prescribe how to combine the DEA therapy with the state of the art surgery protocols.

In a preferred embodiment of the invention, DEA may be used in conjunction with other chemotherapeutic protocols. Standard protocols may be adapted easily by the person skilled in the art to combine the DEA therapy with the state of the art regimens.

In certain other embodiments, DEA provides a suitable adjunct to enhance efficacy of a specific chemotherapy regimen (Temozolomide, Nab-paclitaxel, Paclitaxel, Carmustine (also known as BCNU) Cisplatin) in models of metastatic melanome (B16F10 cell line) by reducing cancer stem cell formation determined from significantly reduced spheroid number, and decreased the number of cells with CD133, CD24 and CD44 cancer stem cell markers.

In certain other embodiments, DEA provides a suitable adjunct to enhance efficacy of chemotherapy (Temozolomide, Nab-paclitaxel, Paclitaxel, Carmustine (also known as BCNU) Cisplatin) in models of metastatic bladder cancer (T24 cell line) by reducing cancer stem cell formation determined from significantly reduced spheroid number, and decreased the number of cells with CD133, CD24 and CD44 cancer stem cell markers.

In certain other embodiments, DEA provides a suitable adjunct to enhance efficacy of chemotherapy (Docetaxel, Paclitaxel, Platinum agents) in models of breast cancer (4T1 mouse mammary carcinoma cell line) by reducing cancer stem cell formation determined from significantly reduced spheroid number, and decreased the number of cells with CD133, CD24 and CD44 cancer stem cell markers.

In certain other embodiments, DEA provides a suitable adjunct to enhance efficacy of chemotherapy (Gemcitabine, 5-fluorouracil (5-FU), Oxaliplatin, Albumin-bound paclitaxel, Cisplatin, Paclitaxel, Docetaxel) in models of pancreas cancer (Panc-1 cell line) by reducing cancer stem cell formation determined from significantly reduced spheroid number, and decreased the number of cells with CD133, CD24 and CD44 cancer stem cell markers.

The administration of DEA or the pharmaceutical formulations comprising thereof is carried out by conventional means. It is readily within the capabilities of the person skilled in the art to determined the appropriate administration for any given circumstances. As a way of non-limiting examples, DEA may be administered subcutaneously, intraperitoneally, intravenously, intravesically, intraarterially, intramedullarly, intrathecally, transdermally, transcutaneously, intranasally, topically, enterealy, intravaginally, sublingually or rectally.

In a preferred embodiment, DEA may be administered intravenously.

In another preferred embodiment, DEA may be administered orally. Oral administration may involve swallowing, so that the compound enters the gastrointestinal tract, or buccal or sublingual administration may be employed by which the compound enters the blood stream directly from the mouth.

Formulation for delivering DEA may include any pharmaceutically acceptable salts, hydrates and solvates thereof, together with a pharmaceutically acceptable excipient, vehicle and/or carrier. The person skilled in the art will have no difficulty to produce suitable formulations using his general knowledge in the field For guidance, see e.g. Remington's Pharmaceutical Sciences (Mack Publishing Company, N.J. 1991). DEA and common pharmaceutical ingredients are available from commercial sources.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Solid formulations for oral administration may be formulated to be immediate and/or modified release.

Modified release formulations include delayed-, sustained-, pulsed-, controlled-, targeted and programmed release.

Further, the pharmaceutical formulations of the invention may also be administered directly into the blood stream, into muscle, or into an internal organ.

For the purposes of the present invention, especially for the administration to human patients, the total daily dose of the compound of the invention is typically in the range from about any of 10 mg/kg to 25 mg/kg to 50 mg/kg to 100 mg to 150 mg/kg to 200 mg to 250 mg/kg or more, depending, of course, on the mode of administration. For example, the compound of the invention may be administered at about 10 mg/kg, 25 mg/kg, 50 mg/kg, 100 mg, 150 mg, 200 mg or 250 mg/kg.

The total daily dose may be administered in single or divided doses and may, at the physician's discretion, fall outside of the typical range given herein. Several dosage regimens may be useful, depending on the pattern of pharmacokinetic decay that the physician wishes to achieve. The dosing regimen can vary over time.

These dosages are based on an average human subject having a weight of about 65 kg to 70 kg. The physician will readily be able to determine doses for subjects whose weight falls outside this range. The precise effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician.

EXAMPLE 1: MATERIALS AND METHODS

Figure 1:
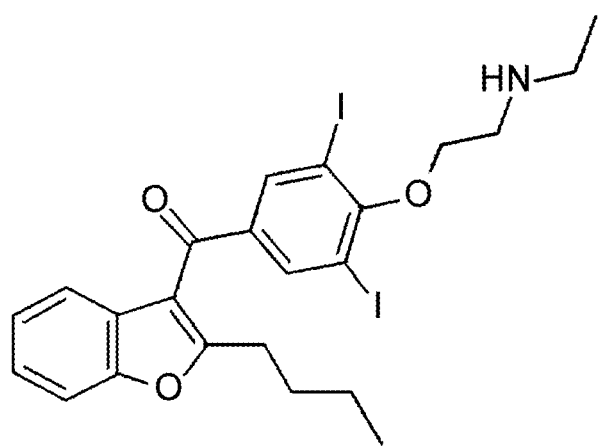
FIG. 1. Structure of desethylamiodarone.

Materials.

Protease inhibitor cocktail, and all chemicals for cell culture were purchased from Sigma-Aldrich Kft (Budapest, Hungary). Desethylamiodarone (DEA) was a gift from Professor Andras Varro (Department of Pharmacology and Pharmacotherapy, University of Szeged, Szeged, Hungary.) The following antibodies were used: anti-Akt, anti-phospho-Akt, anti-phospho-glycogen synthase kinase-3β (GSK), anti-ERK, anti-Phospho-ERK (Cell Signaling, 1:1000), anti-rabbit IgG (Sigma-Aldrich Kft).

Cell Viability Assay.

The cells were seeded into 96-well plates at a starting density of 104 cells per well and cultured overnight before DEA was added to the medium for 24 h and 48 h. The medium was changed to a fresh one containing 0.5% of 3-[4,5-dimethylthiazol-2-yl]-2,5-diphenyl-tetrazolium bromide (MTT+) for an additional 3 hours, then the MTT+ reaction was terminated by adding HCl to 10 mM final concentration. The amount of blue formazan dye formed from MTT+ was proportional to the number of live cells, and was determined with an Anthos Labtech 2010 ELISA reader at 550 nm. All experiments were run in at least 4 replicates and repeated 3 times.

Effect of Desethylamiodarone on Colony Formation.

Cells were trypsinized and plated in triplicate into 6-well plates at 500 cells/well. Cells were treated with different concentration of Dea. After 7 days of incubation, cells were washed and stained with Coomassie-blue, and the colonies containing more than 50 cells were counted. The number of colonies were determined and normalized to the number of colonies in controls.

Mouse Model of Lung Metastasis.

To produce experimental metastasis model, male C57BL/6 mice (6 weeks old) were used. B16F10 cells (5×105/0.1 ml) were injected into the lateral tail vein of C57BL/6 mice, using a 30G1/2 needle and a 1-mL syringe. Mice were randomly divided into 3 groups of 6 mice each. Each mouse was given a daily intragastric injection of either 100 μl 15% ethanol solution as the vehicle control or 25 mg/kg DEA. Treatment was started 1 day before cell injection and was given every third day, lasted for consecutive 16 days Sixteen days after injection, the animals were weighed and killed. The lungs were removed, rinsed in PBS, and weighed. The lung weight index was calculated as the ratio of lung weight vs body weight. The harvested lungs were fixed in 4% formalin. Tumor foci on the surfaces of the lungs were counted under a stereomicroscope. Then, the whole lung was embedded in optimum cutting temperature compound (Sakura Finetek, SA), sectioned (12 mm thickness, 5 levels), and stained with hematoxylin and eosin (H&E) according to routine protocols. Histological observations were performed under a microscope (BX51, Olympus, Japan). The percentage of total area of the stained sections occupied by tumor was measured using the Panoramic viewer 1.15.4 (3DHISTECH, Hungary)

Ethics.

Animal experiments were conducted in strict accordance with the recommendations in the Guide for the Care and Use of Laboratory Animals published by the U.S. National Institutes of Health (NIH Publication No. 85-23, revised 1996), and was approved by the Animal Research Review Committee of the University of Pecs, Medical School.

Western Blot Analysis.

$10^6$ cells were seeded into regular plates and treated as for the cell viability assay. Cells were harvested at intervals in a chilled lysis buffer containing 0.5 mM sodium-metavanadate, 1 mM ethylenediaminetetraacetic acid (EDTA) and protease inhibitor cocktail in phosphate-buffered saline (PBS). Probes were boiled and subjected to 10% sodium dodecyl sulphate polyacrylamide gel electrophoresis then transferred to nitrocellulose membranes. The membranes were blocked in 5% low fat milk for 1.5 h at room temperature then exposed to primary antibodies at 4° C. overnight in blocking solution. Appropriate horseradish peroxidase-conjugated secondary antibodies were used at a 1:5000 dilution (anti-mouse and anti-rabbit IgGs; Sigma-Aldrich, Steinheim, Germany) and visualized by enhanced chemiluminescence (Amersham Biosciences, Piscataway, N.J., USA). All experiments were repeated 3 times.

The Effects of a DEA on the Effectiveness of Radiotherapy.

Cells were trypsinized and plated in triplicate into 6-well plates at 500 cells/well. Cells were treated with different concentration of DEA and irradiated with a dose of 1.0 and 2.0 Grays. A telecobalt (Therathron 780 C) external irradiation equipment (average photon energy of 1.25 MeV) will be applied for irradiating cells. After 7 days of incubation, cells were washed and stained with Coomassie-blue, and the colonies containing more than 50 cells were counted. The number of colonies were determined and normalized to the number of colonies in controls.

EXAMPLE 2. INHIBITORY EFFECTS OF DESETHYLMAIODARONE ON VIABILITY AND PROLIFERATION ON TUMOR CELL LINES

The effect of desethylamiodarone was measured in T24 (human urinary bladder carcinoma), A549 (human lung adenocarcinoma epithelial), B16F10 (mice melanoma), HeLa (human cervix adenocarcinoma), 4T1 (mouse mammary carcinoma) cell lines. Cells were treated with increasing concentrations of desethylamiodarone for 24 and 48 h. Cell growth was assessed by measuring metabolic activity, which reflects viability in the MTT-test in the course of 24 h, 48 h of continued exposure to desethylamiorarone. The untreated cells served as negative controls. The viability of the cells, was lower in all DEA-treated than in the control group, with the difference being statistically significant. The results showed that DEA significantly inhibited the viability of these tumor cell lines.

Effect of DEA on Viability on T24/83 Human Urinary Bladder Carcinoma Cell Line

T24 cells were exposed for 24 h (A), 48 h (B) to 5 μmol, 10 μM, 15 μM and 15 μM desethylamiodarone (filled bars). Viability of the cells was detected by the MTT+ method. Untreated cells served as controls. Data represent means±S.E.M. of three independent experiments, each running in four replicates. Significantly different from control group at p<0.01.

Figure 2:
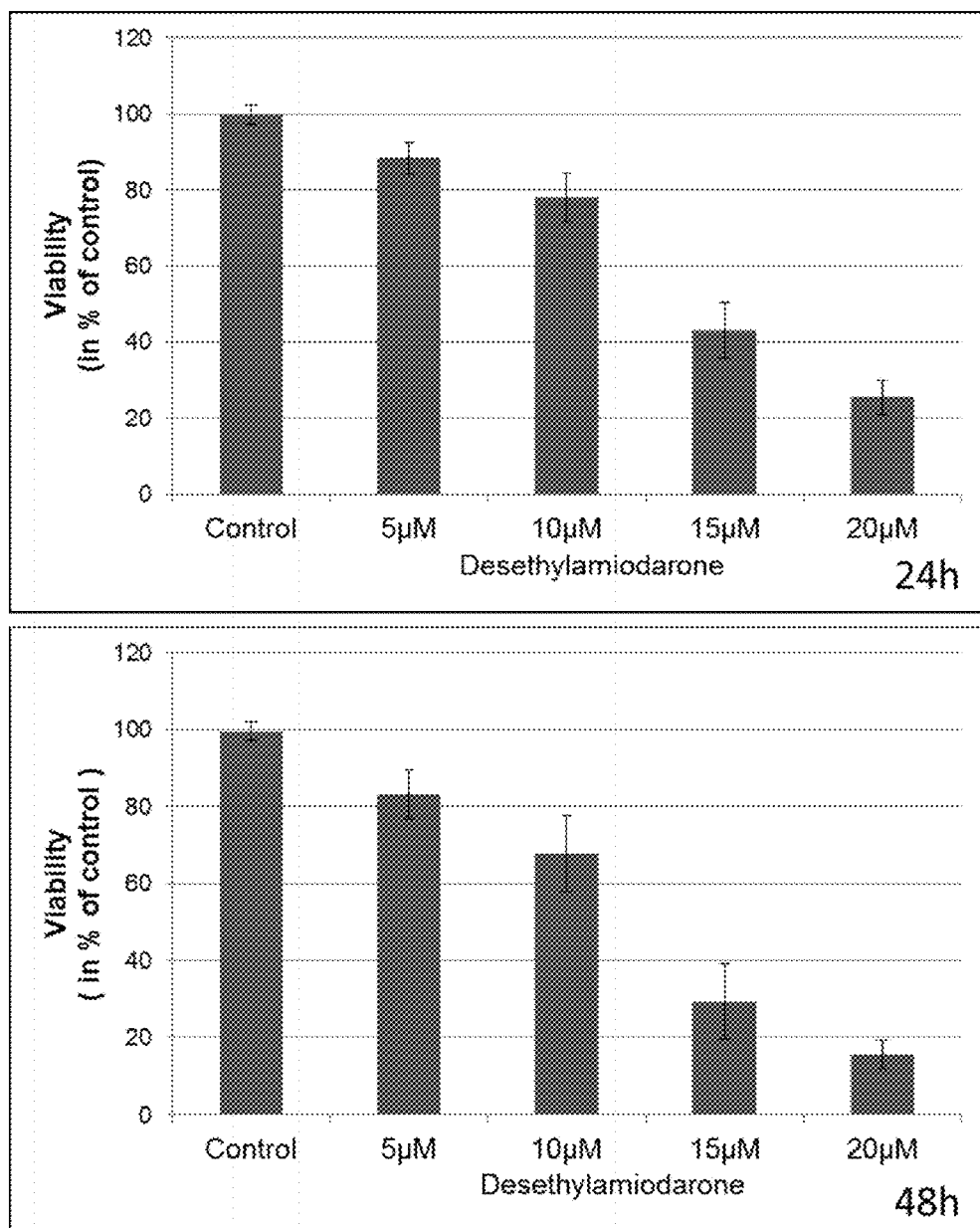
FIG. 2. Effect of Desethylamiodarone on cell death in T24 cells.

The data shown on FIG. 2 provide evidence that DEA can be useful to treat bladder cancer.

Effect of DEA on Viability on B16F10 Mice Melanoma Cell Line

B16F10 cells were incubated with the indicated concentrations (2.5, 5, 7.5 or 10 μM) of desethylamiodarone for 24 h (A) and 48 h (B) and cell viability was measured by MTT assay (filled bars). Untreated cells served as controls. Data represent means±S.E.M. of three independent experiments, each running in four replicates. Significantly different from control group at p<0.01.

Figure 3:
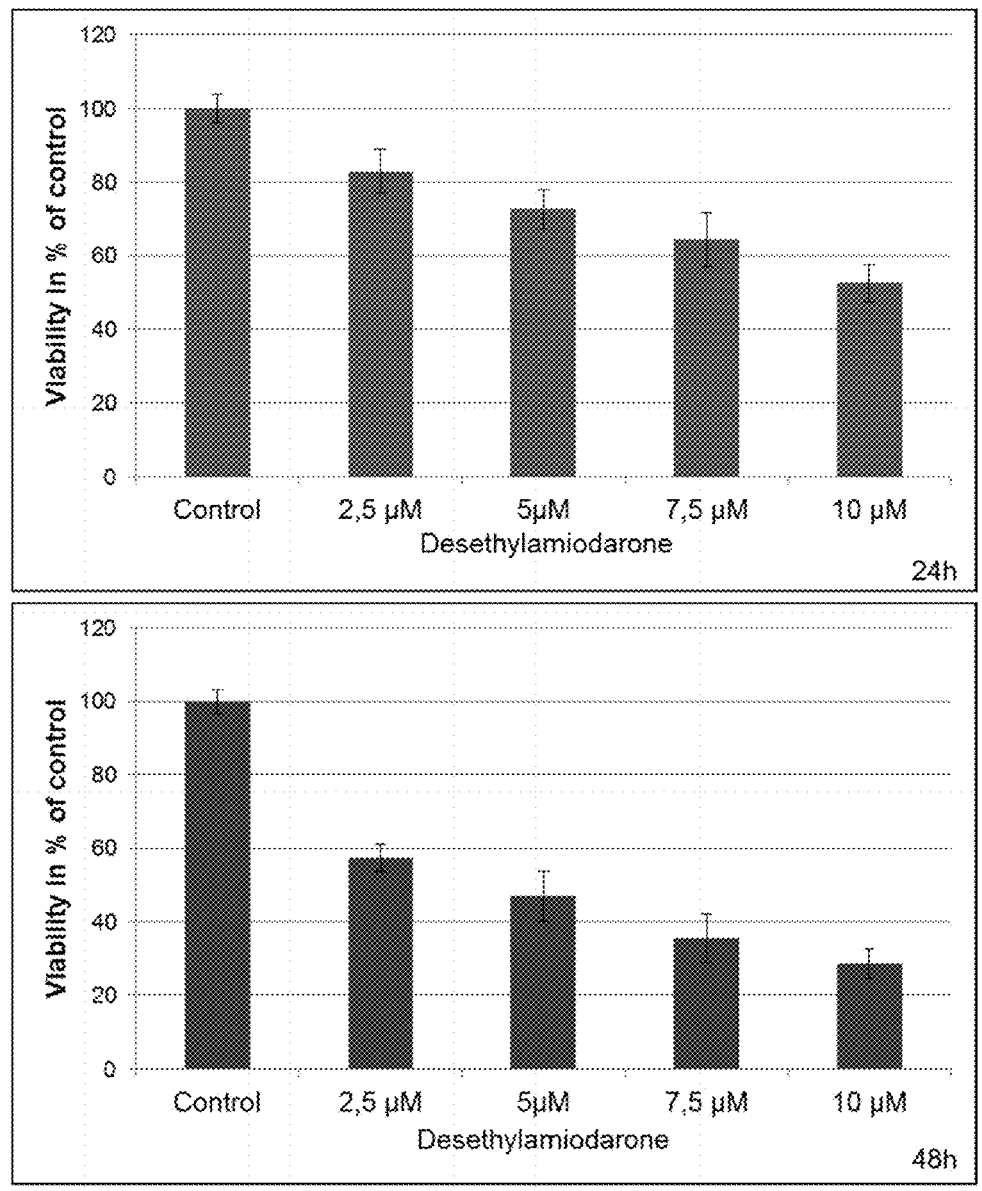
FIG. 3. Effect of Desethylamiodarone on cell proliferation in B16F10 murine melanoma cells.

The data shown on FIG. 3 provide evidence that DEA can be useful to treat melanoma.

Effect of DEA on Viability on 4T1 Mouse Mammary Carcinoma Cell Line

4T1 cells were incubated with the indicated concentrations (2.5, 5, 7.5 or 10 μM) of desethylamiodarone for 24 h and 48 h and cell viability was measured by MTT assay (filled bars). Untreated cells served as controls. Data represent means±S.E.M. of three independent experiments, each running in four replicates. Significantly different from control group at p<0.05.

Figure 4:
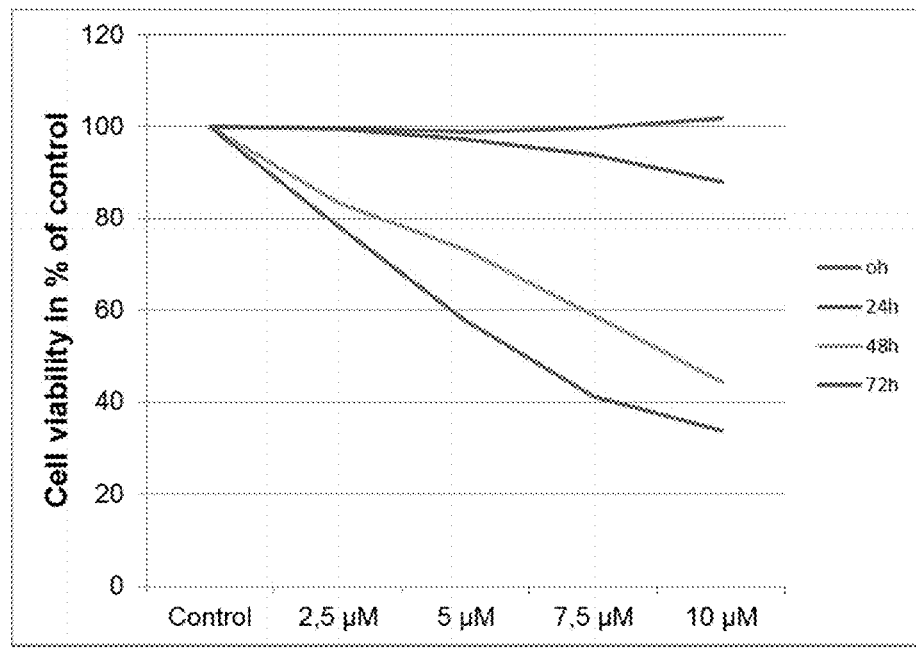
FIG. 4. Effect of Desethylamiodarone on cell proliferation in 4T1 mouse mammary carcinoma cells.

The data shown on FIG. 4 provide evidence that DEA can be useful to treat breast cancer.

Figure 15:
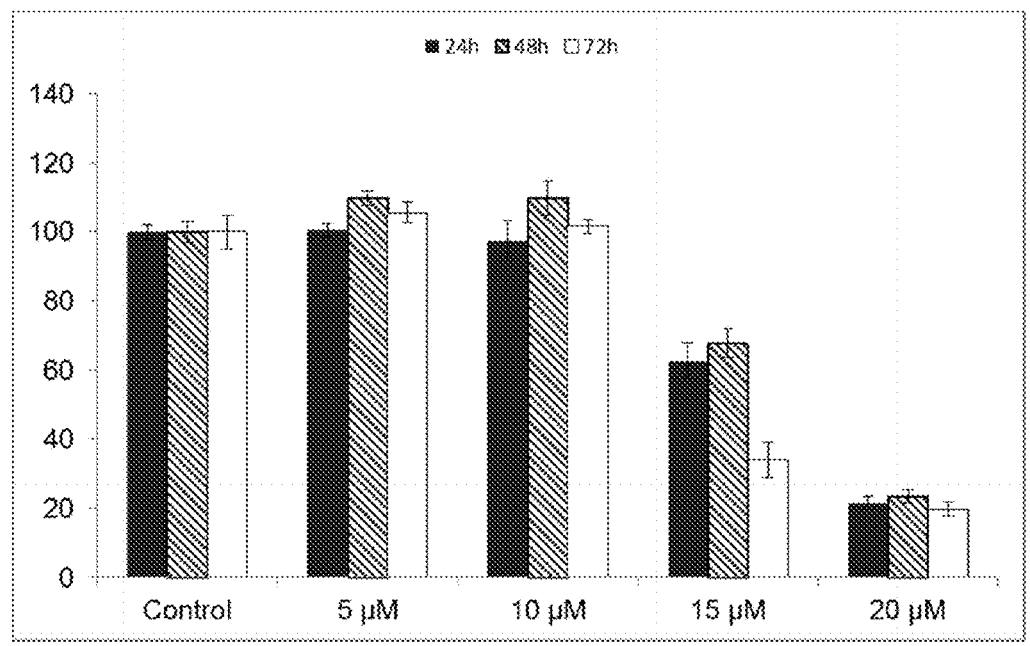
FIG. 15. Effect of DEA on viability on DU-145 prostate cancer cell line.

Effect of DEA on Viability on DU-145 Prostate Cancer Cell Line 145 cells were exposed to increasing concentrations of DEA for 24, 48 and 72 hours. Viability of the cells was detected by the MTT method. Untreated cells served as controls. The data shown on FIG. 15 provide evidence that DEA can induces cell death in DU-145 prostate cancer cell line.

Effect of a DEA on the Effectiveness of Cisplatin Sensitivity of DU-145 Prostate Cancer Cell Line.

DU-145 cells were exposed to increasing concentrations of cisplatin 48 hours in presence or absence of 10 μM DEA. Viability of the cells was detected by the MTT method. Untreated cells served as controls.

Figure 16:
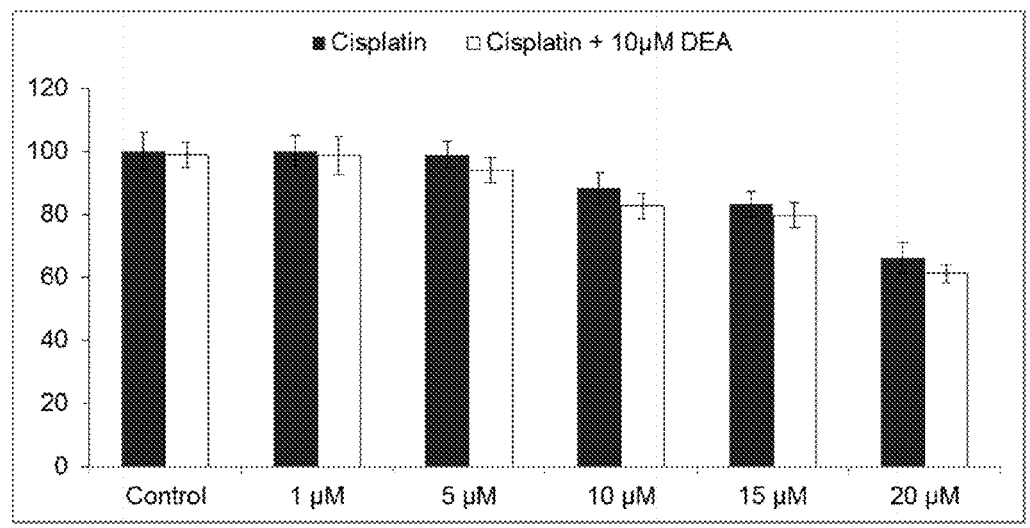
FIG. 16. The effects of a DEA on the effectiveness of cisplatin sensitivity of DU-145 prostate cancer cell line.

The data shown on FIG. 16 provide evidence that DEA sensitizes DU-145 prostate cancer cells for cisplatin.

Effect of a DEA on MCF 7 Breast Cancer Cell Line.

Figure 17:
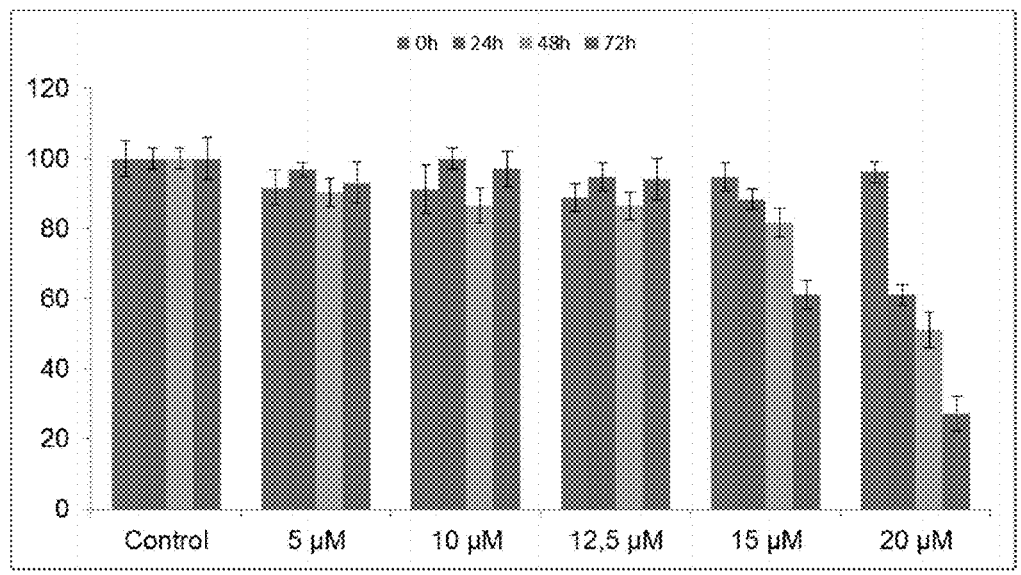
FIG. 17. Effect of DEA on MCF 7 breast cancer cell line.

MCF 7 cells were exposed to increasing concentrations of DEA for 24, 48 and 72 hours. Viability of the cells was detected by the MTT method. Untreated cells served as controls. The data shown on FIG. 17 provide evidence that DEA induces cell death in MCF 7 breast cancer cell line.

EXAMPLE 3. EFFECT OF DESETHYLAMIODARONE ON COLONY FORMATION ON TUMOR CELL LINES

To assess the recovery ability of cells that survived treatment, long-term (7 days) colony formation assay was performed. One week following treatment with desethylamiodarone at the lowest concentrations (500 nM, 1, 2, 2.5 and 3 μM respectively) indicated already a significant decrease in the number and the size of colonies.

Figure 5:
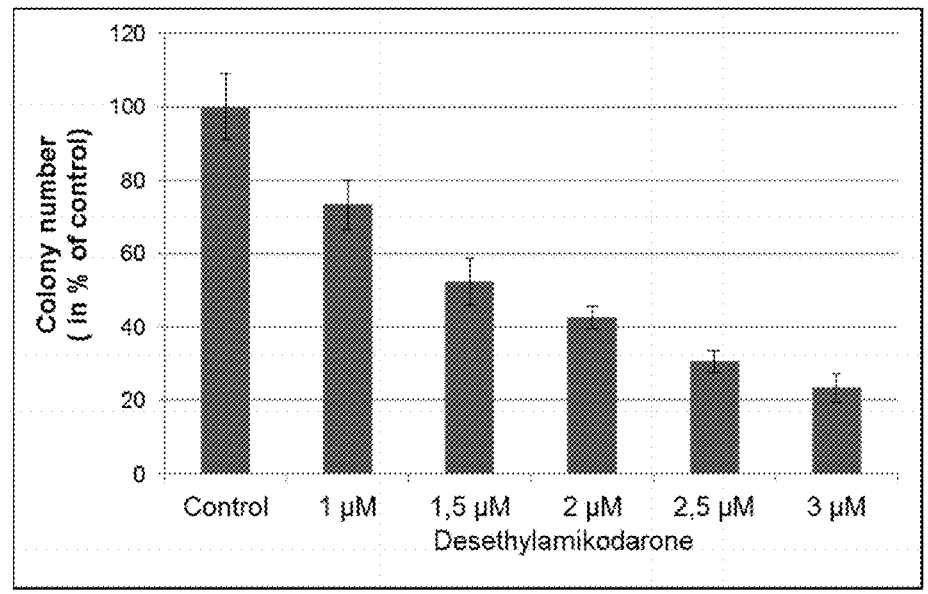
FIG. 5. The effect of treatment with Desethylamiodarone on the colony forming abilities of T24 human bladder cancer cell line.

Effect of Desethylamiodarone on Colony Formation on T24/83 Human Urinary Bladder Carcinoma Cell Line Untreated cells served as controls. The results are mean±SEM of 3 independent experiments performed in at least quadruplicate. p<0.01 compared to the corresponding control group. The data shown on FIG. 5 provide evidence that DEA can be useful to treat bladder cancer.

Figure 6:
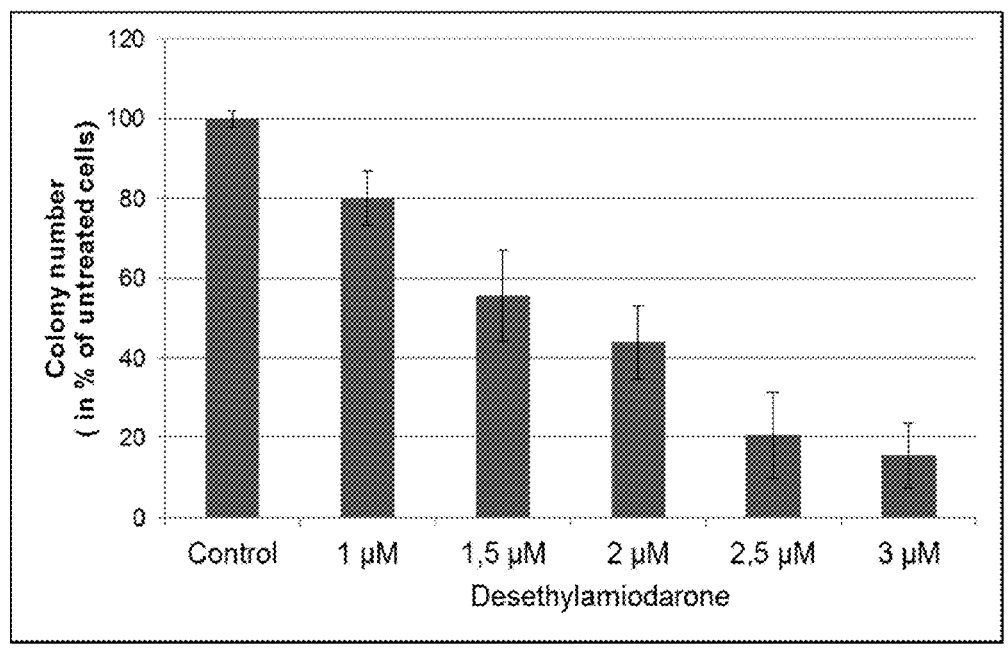
FIG. 6. Inhibition of colony formation in B16F10 cells by desethylamiodarone.

Effect of Desethylamiodarone on Colony Formation on B16F10 Mice Melanoma Cell Line B16F10 cells were incubated with the indicated concentrations of desethylamiodarone (1, 1.5, 2, 2.5 or 3 μM for one week and cell colonies were fixed, stained and counted. (A-B) Data are expressed as the mean±SD of ≥3 experiments; a p<0.01 is considered statistically significant. The data shown on FIG. 6 provide evidence that DEA can be useful to treat melanoma.

Effect of Desethylamiodarone on Colony Formation on A549 Human Lung Adenocarcinoma Epithelial Cell Line A549 cells were incubated with the indicated concentrations of desethylamiodarone (1, 1.5, 2, 2.5 or 3 μM for one week and cell colonies were fixed, stained and counted. (A-B) Data are expressed as the mean±SD of ≥3 experiments; a p<0.01 is considered statistically significant.

Figure 7:
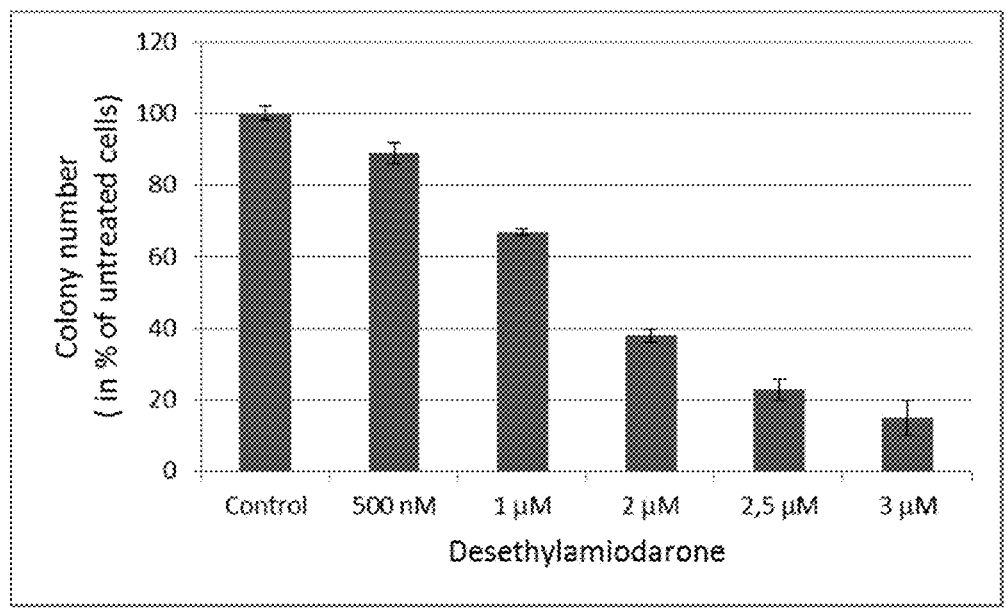
FIG. 7. Inhibition of colony formation in A549 cells by desethylamiodarone.

The data shown on FIG. 7 provide evidence that DEA can be useful to treat lung cancer.

Figure 8:
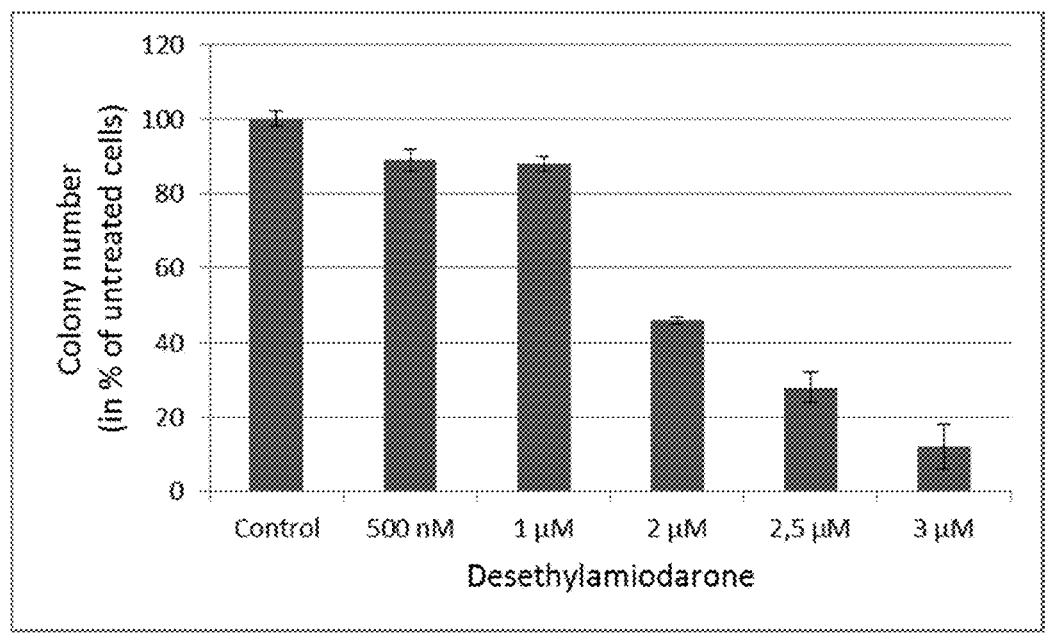
FIG. 8. Inhibition of colony formation in Hela cells by desethylamiodarone.

Effect of Desethylamiodarone on Colony Formation on HeLa Human Cervix Adenocarcinoma Cell Line HeLa cells were incubated with the indicated concentrations of desethylamiodarone (1, 1.5, 2, 2.5 or 3 μM for one week and cell colonies were fixed, stained and counted. (A-B) Data are expressed as the mean±SD of ≥3 experiments; a p<0.01 is considered statistically significant The data shown on FIG. 8 provide evidence that DEA can be useful to cervix carcinoma.

EXAMPLE 4. EFFECT OF DESETHYLAMIODARONE ON LUNG METASTASIS FORMATION OF MELANOMA ON B16F10 MICE MELANOMA CELL LINE

Inhibitory Effects of DEA on Artificial Lung Metastasis.

Figure 9:
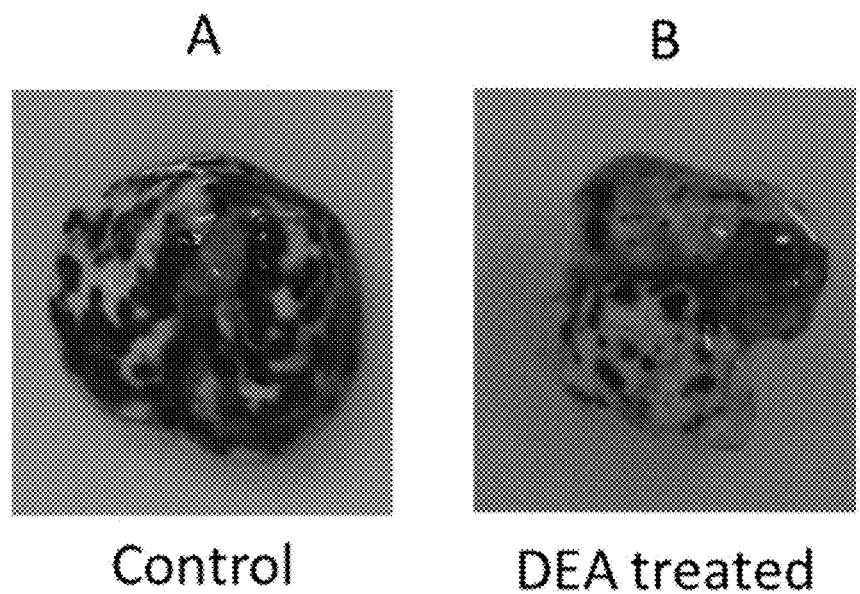
FIG. 9. Inhibitory effects of DEA on artificial lung metastasis.
Figure 9:
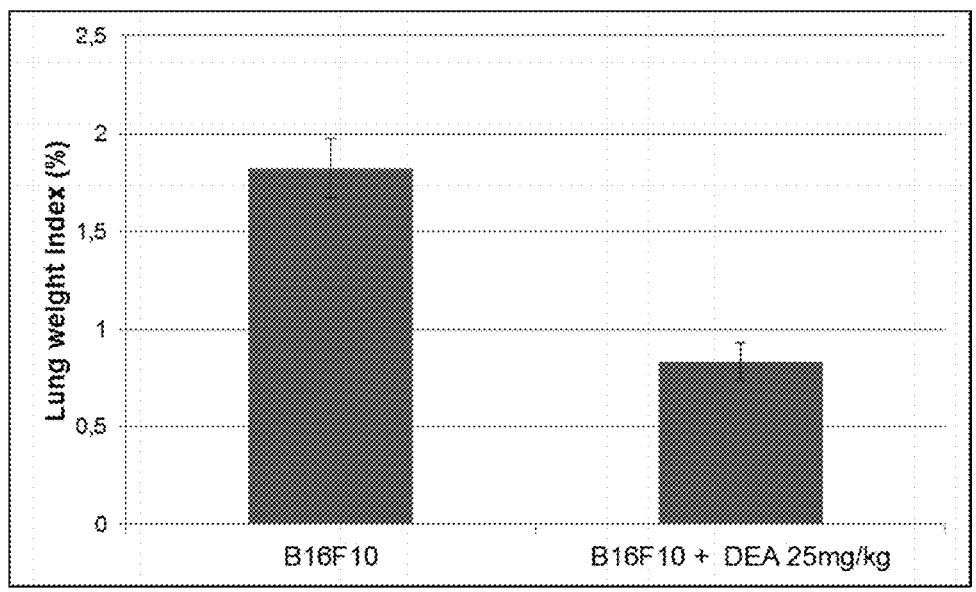
Figure 9:
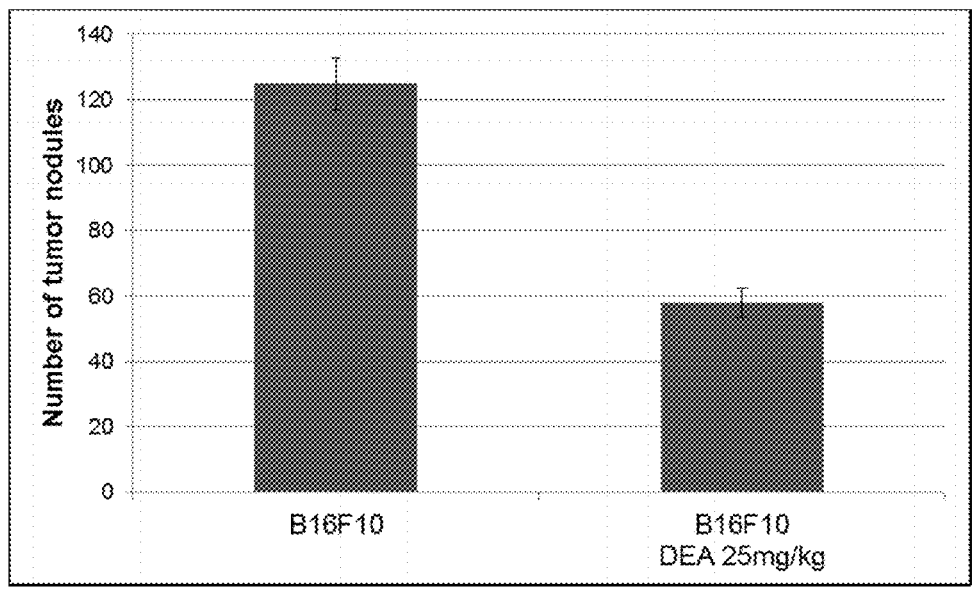

Murine melanoma B16F10 cells were injected into the lateral tail vein of 6-weeks-old male C57BL/6 mice and divided into two groups (6 mice/group). Intraperitoneal administration of 25 mg/kg DEA or vehicle control was started 24 h after tumor cell inoculation, and repeated every third day. The treatment group received desethylamiodarone injection, while the control group received vehicle control treatment. As shown in FIG. 9, desethylamiodarone treatment substantially inhibited tumor appearance. At the 16th day of the experiment lungs were removed for analysis. Lungs were photographed (FIG. 9 A,B), weighted and lung weight index was calculated as the ratio of lung weight versus body weight of host mice, and was compared between the two groups. (FIG. 9 C) Desethylamiodarone treatment significantly *P<0.001 inhibited lung weight increase in B16F10 injected mice. Metastatic nodules on lung surface were counted. A dramatically decrease in the number of tumor nodules was observed in the lungs after desethylamiodarone treatment. This observation was confirmed by the statistical analysis of the number of tumor nodules, which showed that the difference between the model group and the desethylamiodarone-treated mice group was significant *P<0.001. (FIG. 9 D) Accordingly, the lung weight index, and the number of tumor nodules indicated that metastasis was less remarkable for desethylamiodarone treated mice than control group. Lung metastasis in C57BL/6 mice induced from B16F10 tail vein injection. 24 h after injection of melanoma B16F10 cells, mice in the control group were treated with vehicle (alcohol), mice in the treatment group were injected with desethylamiodarone (25 mg/kg, i.p., every 3rd day.) After 16 day's mice were sacrificed and then analyzed. Effect of desethylamiodarone on lung metastasis formation was photographed A and B: mouse with B16F10 lung metastasis vehicle treated or DEA treated, respectively. Lung weight was determined and lung weight index was calculated (C). Tumor growth was monitored also by counting the tumor nodules (D). Treatment caused a statistically significant decrease in metastasis (***P<0.001). Data are presented as the mean±standard deviation. *P<0.001 compared with control.

These data provide evidence that DEA can be useful to inhibit melanoma metastasis.

Histopathology Analysis of Lung Metastasis

Figure 10:
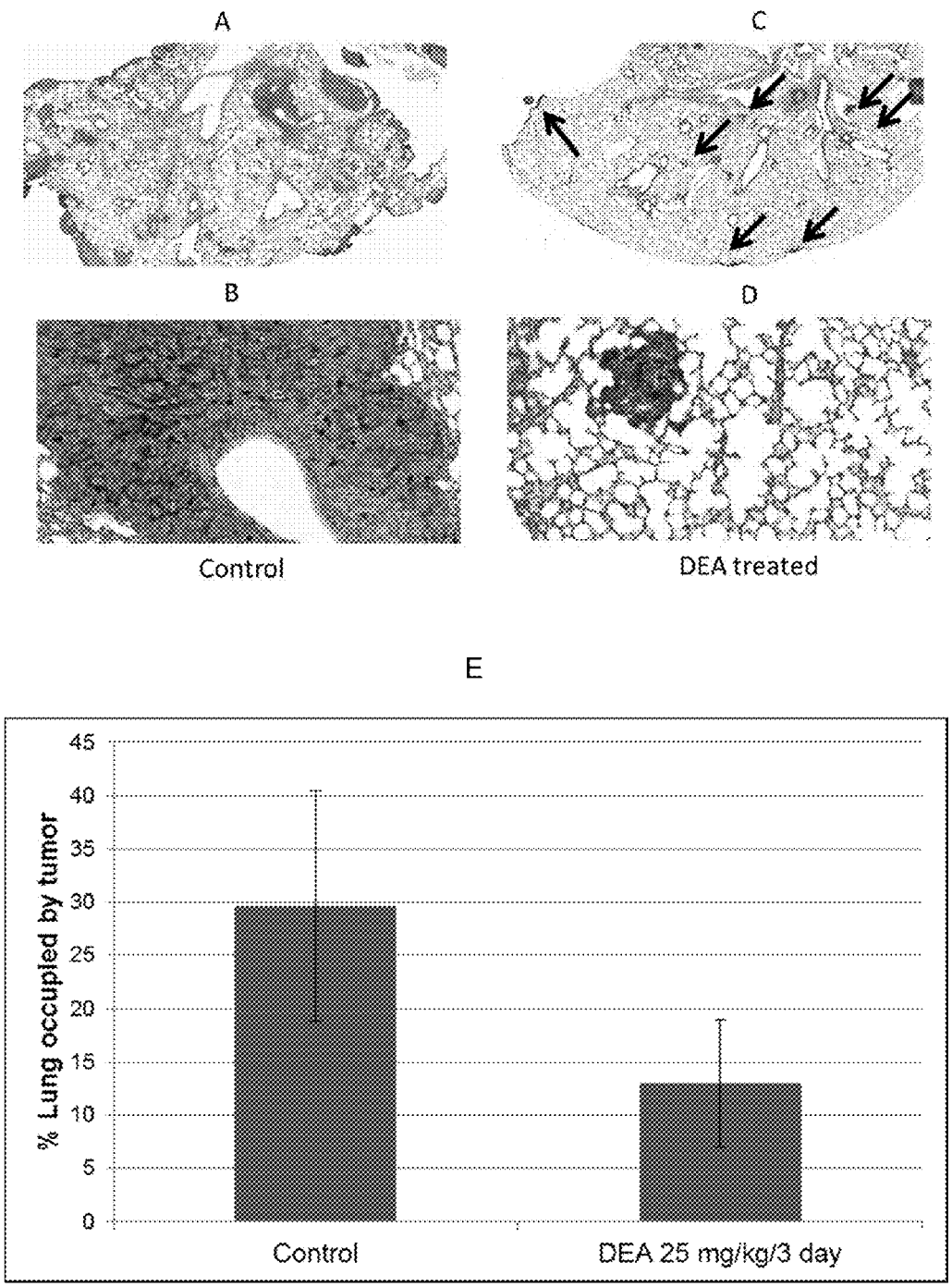
FIG. 10. Histopathology analysis of lung metastasis.

Lungs of the metastasis-induced animals were fixed in neutral buffered formalin and stained with hematoxyline and eosin. Lung tissue sections were analyzed histopathological after H & E staining. Histopathology analysis was made of lung metastasis from mice treated with the vehicle, control (A,C) and of lung metastasis from mice treated with 25 mg/kg/3 days DEA (B,D). Histopathology of the lung also showed marked reduction in tumor mass in the lungs of Desethylamiodarone-treated animals (FIG. 10 A,B,C,D). It showed a difference in tumor nodule pattern distribution, concentration. Image analysis with the Panoramic Viewer Imaging System results quantifying percentage coverage of tumor area over lung section area n=6 per group. (E) Data are reported as means±SD. **P<0.001, unpaired Student t-test, n=6. The percentage of tumor area was determined in comparison to total section area (FIG. 10 E). The percentage of tumor area was significantly decreased in HE stained sections *p<0.001. From a structural point of view, it was observed that melanoma cells with poliedric morphology with a great amount of melanin content as cytoplasm granules or in a perinuclear distribution. Additionally, aberrant nodular proliferation in Broncho alveolar regions, characteristic of epithelial melanoma, was observed (FIG. 10A,C). After desethylamiodarone treatment (FIG. 10 B,D) tumor nodules were decreased and organized in a predominantly in the lung parenchymal distribution, whereas, in control group, the nodules were larger and distributed in all part of the lung. The results are in accordance with those of macroscopic observations. This result indicates that DEA can inhibit in vivo melanoma tumor metastasis.

These data provide evidence that DEA can be useful to inhibit melanoma metastasis.

EXAMPLE 5. SENSITIZATION OF CANCER CELLS TO IRRADIATION

Sensitizing cancer cells to irradiation is a major challenge in clinical oncology therefore we used DEA to demonstrate its radiosensitizing effects. To examine the effects of a DEA on the effectiveness of radiotherapy the cells were treated with 1Gy or 2Gy single dose irradiation alone or combined with 500 nM-3 µM DEA. DEA treatment significantly increases the effectiveness of Radiotherapy.

The Effects of a DEA on the Effectiveness of Radiotherapy on the Colony Forming Abilities of T24 Human Bladder Cancer Cell Line.

The cells were treated with 1Gy or 2Gy single dose irradiation alone or combined with 500 nM-3 µM DEA. Untreated cells served as controls. The results are mean±SEM of 3 independent experiments performed in at least quadruplicate. P<0.05 compared to the corresponding control group.

Figure 11:
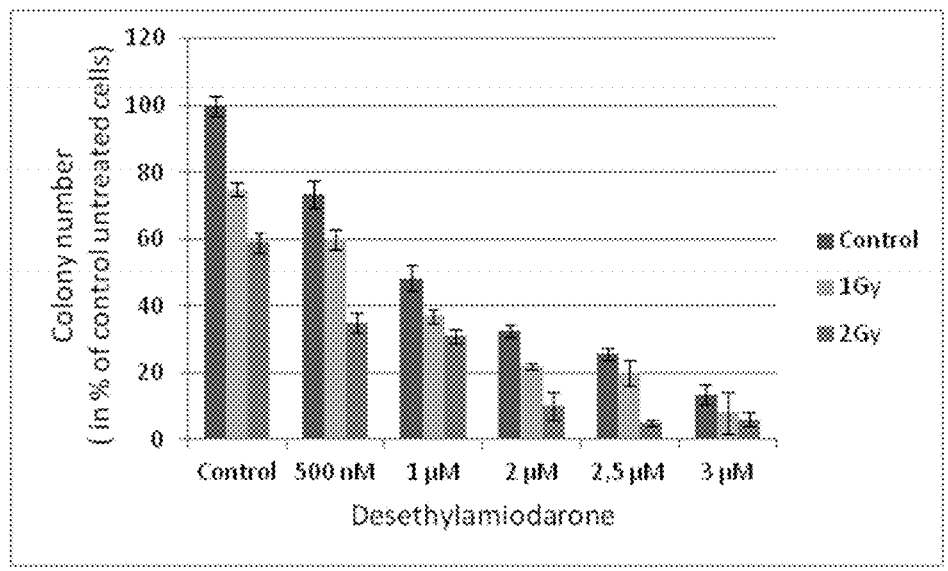
FIG. 11. The effects of a DEA on the effectiveness of radiotherapy on the colony forming abilities of T24 human bladder cancer cell line.

The data shown on FIG. 11 provide evidence that DEA can be useful to sensitize bladder cancer to irradiation The Effects of a DEA on the Effectiveness of Radiotherapy on the Colony Forming Abilities of A549 Human Lung Adenocarcinoma Epithelial Cell Line.

The cells were treated with 1Gy or 2Gy single dose irradiation alone or combined with 500 nM-3 µM DEA. Untreated cells served as controls. The results are mean±SEM of 3 independent experiments performed in at least quadruplicate. p<0.05 compared to the corresponding control group.

Figure 12:
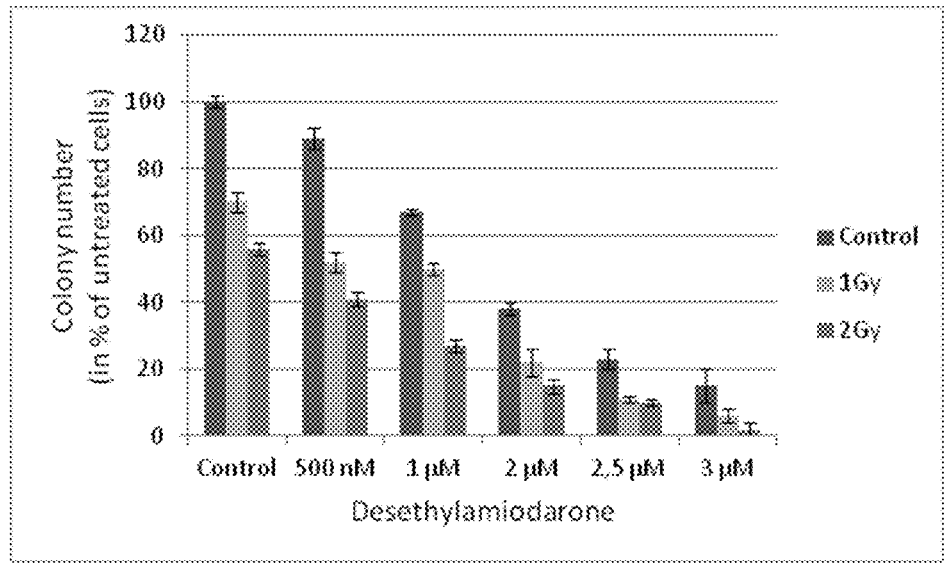
FIG. 12. The effects of a DEA on the effectiveness of radiotherapy on the colony forming abilities of A549 human lung adenocarcinoma epithelial cell line.

The data shown on FIG. 12 provide evidence that DEA can be useful to sensitize lung cancer to irradiation The Effects of a DEA on the Effectiveness of Radiotherapy on the Colony Forming Abilities of HeLA Human Cervix Adenocarcinoma Cell Line.

The cells were treated with 1Gy or 2Gy single dose irradiation alone or combined with 500 nM-3 µM DEA. Untreated cells served as controls. The results are mean±SEM of 3 independent experiments performed in at least quadruplicate. p<0.05, compared to the corresponding control group.

Figure 13:
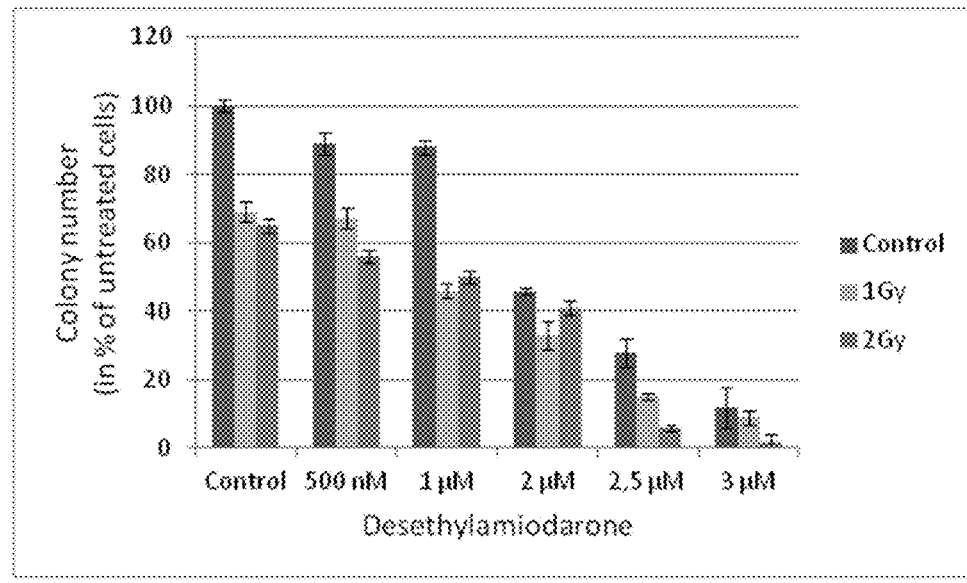
FIG. 13. The effects of a DEA on the effectiveness of radiotherapy on the colony forming abilities of HeLA human cervix adenocarcinoma cell line.
Figure 14:
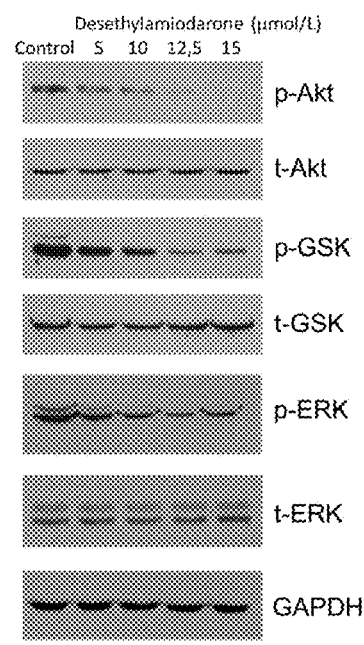
FIG. 14. Effect of desethylamiodarone on Akt, GSK-3β and ERK pathways in T24 cell line.

The data shown on FIG. 13 provide evidence that DEA can be useful to sensitize cervix cancer to irradiation The Effects of a DEA on the Effectiveness of Radiotherapy of MCF 7 Breast Cancer Cells.

MCF 7 cells were exposed to 2Gy irradiation for 24, 48 and 72 hours in presence or absence of increasing concentration of DEA. Viability of the cells was detected by the MTT method. Untreated cells served as controls.

Figure 18:
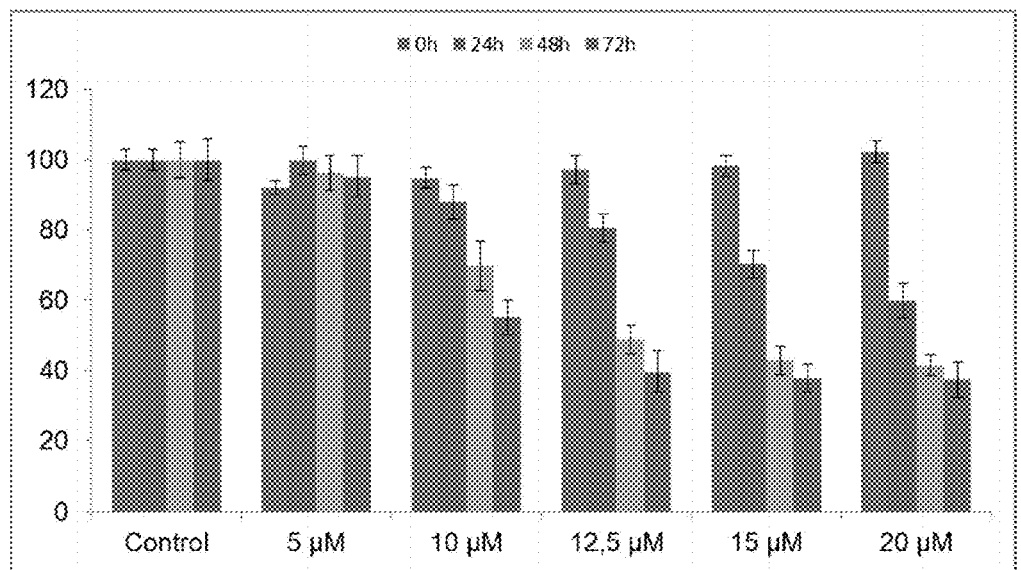
FIG. 18. The effects of a DEA on the effectiveness of radiotherapy of MCF 7 breast cancer cells.

The data shown on FIG. 18 provide evidence that DEA can be useful to sensitize MCF 7 breast cancer cells to irradiation.

EXAMPLE 6. THE EFFECT OF DESETHYLAMIODARONE ON KEY SIGNALING PATHWAYS

To determine the downstream consequences of DEA treatment, we examined the phosphorylation status of AKT (protein kinase B), GSK-3β and p42/44 mitogen-activated protein kinase (MAPK) (ERK1/2) by immunoblotting in T24 (human urinary bladder carcinoma), B16F10 (mice melanoma) cell lines. Cells were cultured in the presence of 5-10-15 µM DEA for 6 hours. The cells were prepared and western blot analysis was carried out to perform both phosphorylated and non-phosphorylated forms of the previously listed proteins. Analyzing the activity of the protein ERK, commonly involved in tumor proliferation, we found a decrease in its phosphorylation after 6 hours of treatment with 5-10-15 µM DEA. Since previous reports have indicated that the PI3K/Akt pathway provides a survival signal to protect cells from apoptosis (26), we determined the effect of DEA treatment on the activity of Akt. We observed that DEA repressed Akt (Ser473) phosphorylation in a concentration-dependent manner (FIG. 12). We extended our observations to evaluate whether AKT downstream target GSK-3β was affected. DEA treatment also decreased the phosphorylation of GSK-3β after 6 hours at a concentration dependent manner. These results indicate that the efficacy of this drug could be related with the modulation of ERK1/2, AKT, and GSK-3β proteins.

EXAMPLE 7. THE EFFECT OF DESETHYLAMIODARONE ON CSC SUBPOPULATION

The CSC hypothesis is an important concept arising in cancer research. This hypothesis postulates the existence of a subgroup of cancer cells, the CSCs, which has the ability to self-renew and to differentiate into all cell types of the original heterogeneous tumor, thus resembling the function of normal epithelial stem cells.

To efficiently treat cancer, it is important to target the CSCs, ideally in combination therapies that also target the bulk of the tumor. To examine the effect of DEA on the cancer stem cell populations, we carried out flow cytometry using the cancer stem cell markers (CD44+/CD24−/low).

Desethylamiodarone treatment will be tested for decreasing the CD44+ cell population and decreasing the incidence of CSC cells.

EXAMPLE 8. THE EFFECT OF DESETHYLAMIODARONE ON CSC SUBPOPULATION

T24 cells were exposed to 5, 10 and 15 µM of DEA for 24 h intervals. Equal amounts of lysate protein were subjected to gel electrophoresis. GAPDH was used as loading control. Results are presented as representative immunoblots (top panel) and densitometric analysis of Western blots in bar diagrams (bottom graph). Data are expressed as the mean±1 SD, n=3 and presented as fold difference from control (medium). Significant difference from control: *p<0.05.

Figure 19:
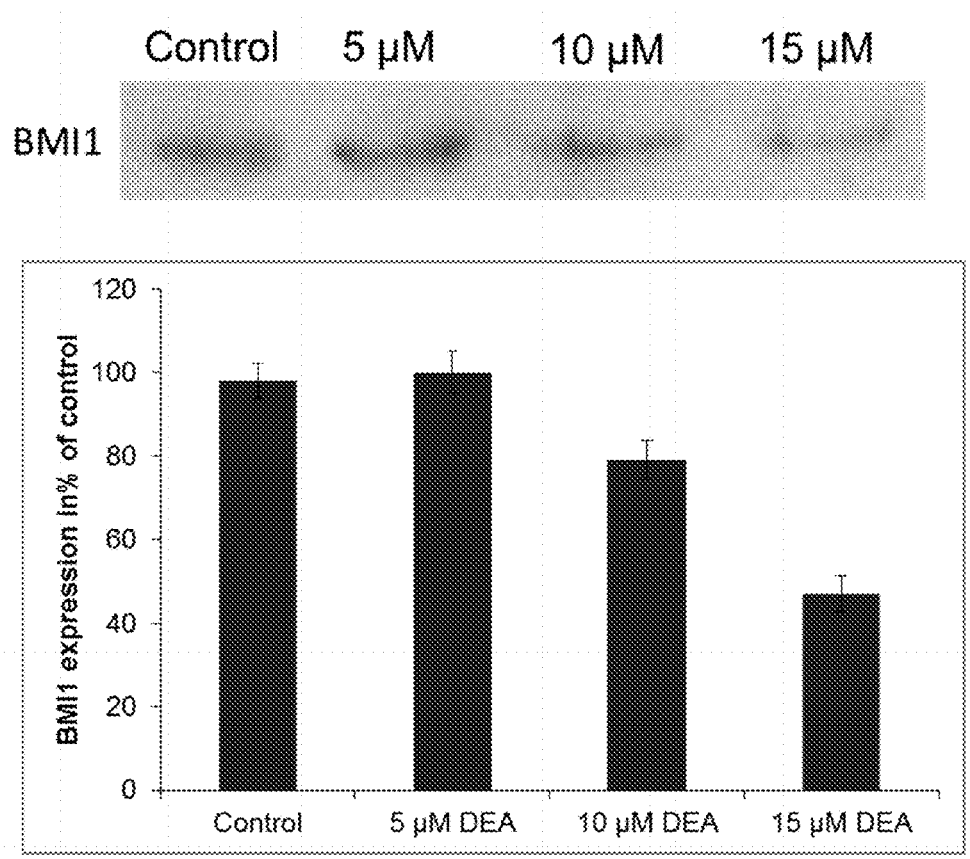
FIG. 19. The effects of a DEA on BMI1 expression in T24 human bladder cancer cells.

The data shown on FIG. 19 provide evidence that DEA significantly suppresses BMI1 expression in T24 human bladder cancer cells.

REFERENCES

1. Pallandi R T and Campbell T J.: Resting and rate-dependent depression of Vmax of guinea-pig ventricular action potentials by amiodarone and desethylamiodarone. Br J Pharmacol 92: 97-103; 1987.
2. Nattel S., Talajic M., Quantz M and DeRoode M.: Frequency-dependent effect of amiodarone on atrioventricular nodal function and slow-channel action potentials: evidence for calcium channel-blocking activity. Circulation 76: 442-449; 1987.
3. Szabados E, Literati N P, Farkas B, Sumegi B.: BGP-15, a nicotinic amidoxime derivate protecting heart from ischemia reperfusion injury through modulation of poly (ADP-ribose) polymerase. Biochem Pharmacol 2000; 59:937-945.
4. Leeuwenburgh B P., Versteegh M I., Maas J J., Dunning J.: Should amiodarone or lidocaine be given to patients who arrest after cardiac surgery and fail to cardiovert from ventricular fibrillation? Interact Cardiovasc Thorac Surg. 2008 December; 7(6):1148-51. doi: 10.1510/icvts.2008.188656. Epub 2008 Sep. 16.
5. Hughes M., Binning A.: Intravenous amiodarone in intensive care. Time for a reappraisal? Intensive Care Med. 2000 December; 26(12):1730-9.
6. Lalloz M R A, Byfield P G H, Greenwood R M, Himsworth R L.: Binding of amiodarone by serum proteins and the effects of drugs, hormones and other interacting ligands. J Pharm Pharmacol. 1984; 36:366-372.
7. Nokin P. Clinet M and Schoenfeld P.: Cardiac □-adrenoreceptor modulation by amiodarone. Biochem Pharmacol 32:2473-2477; 1983.
8. Daniels J M., Brien J F and Massey T E.: Pulmonary fibrosis induced in the hamster by amiodarone and desethylamiodarone. Toxicol Appl Pharmacol 100: 350-359; 1989.
9. Vander E L., Goudemant J F., Mouton J., Chatelain P., Van Haverbeke Y., Muller R N.: Amiodarone pretreatment effects on ischemic isovolumic rat hearts: a P-31 nuclear magnetic resonance study of intracellular pH and high-energy phosphates contents evolutions. J Cardiovasc Pharmacol. 1990 March; 15(3):377-85.
10. Lapinsky S E., Mullen J B., Baiter M S.: Rapid pulmonary phospholipid accumulation induced by intravenous amiodarone Can. J. Cardiol., 9 (1993), pp. 322-324
11. Holt D W., Tucker G T., Jackson P R., McKenna W J.: Amiodarone pharmacokinetics. Br J Clin Pract Suppl. 1986 April; 44:109-14.
12. Brien J F., Jimmo S., Brennan F J., Armstrong P W., Abdollah H.: Disposition of amiodarone and its proximate metabolite, desethylamiodarone, in the dog for oral administration of single-dose and short-term drug regimens. Drug Metab Dispos. 1990 November-December; 18(6):846-51.
13. Honegger U E., Zuehlke R D., Scuntaro I., Schaefer M H., Toplak H., Wiesmann U N.: Cellular accumulation of amiodarone and desethylamiodarone in cultured human cells. Consequences of drug accumulation on cellular lipid metabolism and plasma membrane properties of chronically exposed cells. sinBiochem Pharmacol. 1993 Jan. 26; 45(2):349-56.
14. Singh B N. and Vaughan Williams E M.: The effect of amiodarone, a new anti-anginal drug, on cardiac muscle. Br J Pharmacol 39:657-67; 1970.
15. Hostetler K Y., Reasor M J., Walker E R., Yazaki P J., Frazee B W.: Role of phospholipase A inhibition in amiodarone pulmonary toxicity in rats. Biochim Biophys Acta. 1986 Feb. 12; 875(2):400-5.
16. Staubli M., Bircher J., Galeazzi R L., Remund H., Studer H.: Serum concentrations of amiodarone during long term therapy. Relation to dose, efficacy and toxicity. Eur J Clin Pharmacol. 1983; 24(4):485-94.
17. Holt D W., Tucker G T., Jackson P R., Storey G C.: Amiodarone pharmacokinetics. Am Heart J. 1983 October; 106(4 Pt 2):840-7.
18. Mulder J E., Brien J F., Racz W J., Takahashi T., Massey T E.: Mechanisms of amiodarone and desethylamiodarone cytotoxicity in nontransformed human peripheral lung epithelial cells J. Pharmacol. Exp. Ther., 336 (2011), pp. 551-559
19. Roth F C., Mulder J E., Brien J F., Takahashi T., Massey T E.: Cytotoxic interaction between amiodarone and desethylamiodarone in human peripheral lung epithelial cells. Chem Biol Interact. 2013 Aug. 25; 204(3):135-9. doi: 10.1016/j.cbi.2013.05.006. Epub 2013 May 23.
20. Bolt M W., Racz W J., Brien J F., Bray T M., Massey T E.: Effects of vitamin E on amiodarone-induced cytotoxicity in isolated hamster lung cells. Toxicologist 48 (1999) [1-s].
21. Kannan R., Sarma J S., Guha M., Venkataraman K.: Tissue drug accumulation and ultrastructural changes during amiodarone administration in rats. Fundam Appl Toxicol. 1989 November; 13(4):793-803.
22. Eccles S A., Welch D R. Metastasis: recent discoveries and novel treatment strategies. Lancet. 2007; 369:1742-1757. doi: 10.1016/S0140-6736(07)60781-8. [PMC free article] [PubMed] [Cross Ref]
23. Yilmaz M., Christofori G., Lehembre F.: Distinct mechanisms of tumor invasion and metastasis. Trends Mol Med. 2007; 13:535-541. doi: 10.1016/j.molmed.2007.10.004. [PubMed] [Cross Ref]
24. Fidler I J.: The pathogenesis of cancer metastasis: the 'seed and soil' hypothesis revisited. Nat Rev Cancer. 2003; 3:453-458. doi: 10.1038/nrc1098. [PubMed] [Cross Ref]
25. Finn L., Markovic S N., Joseph R W.: Therapy for metastatic melanoma: the past, present, and future. BMC Med. 2012; 10:23. doi: 10.1186/1741-7015-10-23. [PMC free article] [PubMed] [Cross Ref]

26. Fresno Vara J A., Casado E., de Castro J., Cejas P., Belda-Iniesta C., Gonzalez-Baron M.: PI3K/Akt signalling pathway and cancer. Cancer Treat Rev. 2004 April; 30(2):193-204.
27. Varbiro G., Toth A., Tapodi A., Bognar Z., Veres B., Sumegi B., Gallyas F.: Protective effect of amiodarone but not N-desethylamiodarone on postichemic hearts by the inhibition of mitochondrial permeability transition. J. Pharm. Exp. Ther. (2003) 307:615-25.
28. Varbiro, G.; Toth, A.; Tapodi, A.; Veres, B.; Sumegi, B.; Gallyas, F. Jr. Concentration dependent mitochondrial effect of amiodarone. Biochem Pharmacol 65:1115-1128; 2003/2.
29. Zita Bognar, Tamas Kalai, Anita Palfi, Katalin Hanto, Balazs Bognar, Laszlo Mark, Zoltan Szabo, Antal Tapodi, Balazs Radnai, Zsolt Sarszegi, Arpad Szanto, Ferenc Gallyas Jr., Kalman Hideg, Balazs Sumegi, Gabor Varbiro.: A novel SOD-mimetic permeability transition inhibitor agent protects ischemic heart by inhibiting both apoptotic and necrotic cell death. Free Radical Biology & Medicine (2006) 41:835-848
30. Kalai T., Varbiro G., Bognar Z., Palfi A., Hanto K., Bognar B., Osz E., Sumegi B., Hideg K.: Synthesis and evaluation of the permeability transition inhibitory characteristics of paramagnetic and diamagnetic amiodarone derivates. Bioorg. and Med. Chem. (2005) 13:2629-2636.
31. Weiss L.: Metastatic inefficiency. Adv Cancer Res 1990; 54:15.
32. Spano D., Heck C., De Antonellis P., Christofori G., Zollo M.: Molecular networks that regulate cancer metastasis. Semin Cancer Biol. 2012 June; 22(3):234-49. doi: 10.1016/j.
33. Mehlen P., Puisieux A.: Metastasis: a question of life or death Nature Reviews Cancer, 6 (2006), pp. 449-458
34. Monteiro J., Fodde R.: Cancer stemness and metastasis: therapeutic consequences and perspectives European Journal of Cancer, 46 (2010), pp. 1198-1203
35. Benbrook D M., Masamha C P.: The pro-survival function of Akt kinase can be overridden or altered to contribute to induction of apoptosis. Curr Cancer Drug Targets, 2011, 11(5):586-599
36. Desiniotis A., Kyprianou N.: Significance of talin in cancer progression and metastasis. Int Rev Cell Mol Biol. 2011; 289:117-47.
37. Vivanco I., Sawyers C L.: The phosphatidylinositol 3-Kinase AKT pathway in human cancer. Nat Rev Cancer 2002, 2(7):489-501.
38. Arcaro A., S Guerreiro A.: The Phosphoinositide 3-Kinase Pathway in Human Cancer: Genetic Alterations and Therapeutic Implications, Curr Genomics. 2007 August; 8(5): 271-306.
39. Knowles M A., Hurst C D.: Molecular biology of bladder cancer: new insights into pathogenesis and clinical diversity. Nat Rev Cancer. 2015 January; 15(1):25-41. doi: 10.1038/nrc3817.
40. Wu Liang, Dingjun Zhu, Xuejiang Cui, Jiarui Su, Hongwei Liu, Jinli Han, Fengjin Zhao, and Wenlian Xie: Knockdown BMI1 expression inhibits proliferation and invasion in human bladder cancer T24 cells, Mol Cell Biochem. 2013; 382(1-2): 283-291. Published online 2013 Jul. 3. doi: 10.1007/s11010-013-1745-0
41. Siddique H R, Saleem M.: Role of BMI1, a stem cell factor, in cancer recurrence and chemoresistance: preclinical and clinical evidences. Stem Cells. 2012 March; 30(3):372-8. doi: 10.1002/stem.1035.

The invention claimed is:

1. A method for the treatment of cancer, comprising administering a compound selected from the group consisting of desethylamiodarone and pharmaceutically acceptable salts, hydrates and solvates thereof, together with a pharmaceutically acceptable excipient, vehicle and/or carrier to a patient in the need thereof, wherein the compound selected from the group consisting of desethylamiodarone and pharmaceutically acceptable salts, hydrates and solvates thereof, is the sole active ingredient administered to the patient, wherein the cancer is selected from the group consisting of melanoma, breast cancer, cervical cancer, prostate cancer, bladder cancer and lung cancer.

2. The method according to claim 1, wherein the cancer is selected from the group consisting of lung cancer, bladder cancer, melanoma, breast cancer and cervical cancer.

3. The method according to claim 1, further comprising treating the patient with high energy irradiation.

4. The method according to claim 3, wherein the cancer is selected from the group consisting of lung cancer, bladder cancer, melanoma, breast cancer and cervical cancer.

* * * * *